US00RE44803E

(19) United States
(12) Reissued Patent
Masini

(10) Patent Number: US RE44,803 E
(45) Date of Reissued Patent: Mar. 11, 2014

(54) ANTI-IMPINGEMENT FEMORAL PROSTHESES

(75) Inventor: Michael A. Masini, Ann Arbor, MI (US)

(73) Assignee: MedIdea, LLC, Ann Arbor, MI (US)

(21) Appl. No.: 13/491,150

(22) Filed: Jun. 7, 2012

Related U.S. Patent Documents

Reissue of:
(64) Patent No.: 7,985,261
Issued: Jul. 26, 2011
Appl. No.: 10/140,566
Filed: May 7, 2002

U.S. Applications:
(63) Continuation of application No. 09/804,856, filed on Mar. 13, 2001, now Pat. No. 6,383,225, which is a continuation of application No. 09/411,738, filed on Oct. 1, 1999, now Pat. No. 6,200,350.

(51) Int. Cl.
*A61F 2/36* (2006.01)

(52) U.S. Cl.
USPC ..... 623/23.11; 623/22.21; 623/22.42

(58) Field of Classification Search
USPC ..... 623/22.11, 22.15, 22.21, 22.41, 22.44, 623/23.11, 23.35, 23.42
See application file for complete search history.

(56) References Cited

U.S. PATENT DOCUMENTS

| | | | | |
|---|---|---|---|---|
| 3,848,272 | A | 11/1974 | Noiles | 3/1 |
| 4,279,041 | A | 7/1981 | Buchholz | 3/1.912 |
| 4,822,370 | A | 4/1989 | Schelhas | 623/23 |
| 4,908,035 | A | 3/1990 | Deckner et al. | 623/23 |
| 4,938,770 | A | 7/1990 | Frey et al. | 623/23 |
| 4,957,510 | A | 9/1990 | Cremascoli | 623/22.46 |
| 4,978,356 | A | 12/1990 | Noiles | 623/18 |
| 4,978,359 | A | 12/1990 | Wilhelm et al. | 623/23 |
| 5,002,578 | A | 3/1991 | Luman | 623/23 |

(Continued)

FOREIGN PATENT DOCUMENTS

| | | |
|---|---|---|
| EP | 0363019 A2 | 11/1990 |
| EP | 0359672 B1 | 11/1992 |

(Continued)

OTHER PUBLICATIONS

Whiteside et al., Fixation of the Quadralock Femoral Component: A Biomechanical and Clinical Study, Clinical Orthopedics and Related Research, vol. 1 (393), Dec. 2001.

(Continued)

*Primary Examiner* — David Isabella
*Assistant Examiner* — Yashita Sharma
(74) *Attorney, Agent, or Firm* — Gifford, Krass, Sprinkle, Anderson & Citkowski, P.C.

(57) ABSTRACT

A proximal femoral prosthesis minimizes impingement, thereby affording an enhanced range of motion as compared to existing devices. The central portion of the neck of a prosthesis according to the invention is oriented distally relative to a straight line drawn between the ball portion and a point of interconnection to the exposed portion of the stem. Such a configuration reduces impingement in flexion/internal rotation and extension/external rotation, assuming an appropriately placed acetabular component. In the preferred embodiment, the neck is curved between the head and the neck. In alternative embodiments, the neck may be provided in straight and/or modular segments. The invention is compatible with neck-shaft angles, offsets, head sizes, and other dimensions commonly designated with respect to available implants.

8 Claims, 3 Drawing Sheets

(56) References Cited

U.S. PATENT DOCUMENTS

| | | | | |
|---|---|---|---|---|
| 5,002,581 | A | 3/1991 | Paxson et al. | 623/23 |
| 5,030,234 | A | 7/1991 | Pappas et al. | 623/23 |
| 5,030,238 | A | 7/1991 | Nieder | 623/23 |
| 5,047,062 | A | 9/1991 | Pappas et al. | 623/23 |
| 5,080,685 | A | 1/1992 | Bolesky et al. | 623/23 |
| 5,108,452 | A | 4/1992 | Fallin | 623/23 |
| 5,201,882 | A | 4/1993 | Paxson | 623/23 |
| 5,342,363 | A | 8/1994 | Richelsoph | 606/79 |
| 5,358,526 | A | 10/1994 | Tornier | 623/19 |
| 5,387,244 | A | 2/1995 | Breard | 623/23 |
| 5,507,818 | A | 4/1996 | McLaughlin | 623/18 |
| 5,507,819 | A | 4/1996 | Wolf | 623/19 |
| 5,507,830 | A | 4/1996 | DeMane et al. | 623/23 |
| 5,580,352 | A * | 12/1996 | Sekel | 623/22.46 |
| 5,653,764 | A | 8/1997 | Murphy | 623/23 |
| 5,653,765 | A | 8/1997 | McTighe et al. | 623/23 |
| 5,702,480 | A | 12/1997 | Kropf et al. | 623/23 |
| 5,702,484 | A | 12/1997 | Goymann et al. | 623/23 |
| 5,755,805 | A | 5/1998 | Whiteside | 623/22 |
| 5,800,558 | A | 9/1998 | LaHaise, Sr. | 623/23 |
| 5,876,459 | A | 3/1999 | Powell | 623/18 |
| 5,888,207 | A | 3/1999 | Nieder et al. | 623/23 |
| 5,902,340 | A | 5/1999 | White et al. | 623/22 |
| 5,906,644 | A | 5/1999 | Powell | 623/23 |
| 5,916,270 | A | 6/1999 | Lipman | 623/22 |
| 6,139,583 | A | 10/2000 | Johnson | 623/23 |
| 6,200,350 | B1 * | 3/2001 | Masini | 623/23.15 |
| 6,224,634 | B1 * | 5/2001 | Keller | 623/23.11 |
| 6,238,436 | B1 | 5/2001 | Lob et al. | 623/22.42 |
| 6,306,174 | B1 | 10/2001 | Gie et al. | 623/22.42 |
| 6,413,280 | B1 * | 7/2002 | Feiler | 623/22.15 |
| 6,436,147 | B1 | 8/2002 | Zweymuller | 623/22.41 |
| 2002/0038148 | A1 | 3/2002 | Fernandez et al. | 623/23.18 |
| 2002/0052661 | A1 | 5/2002 | Spotorno et al. | 623/23.48 |
| 2002/0058999 | A1 | 5/2002 | Dwyer et al. | 623/22.42 |
| 2002/0059000 | A1 | 5/2002 | Dwyer et al. | 623/22.43 |
| 2002/0120343 | A1 | 8/2002 | Doubler et al. | 623/22.42 |

FOREIGN PATENT DOCUMENTS

| | | |
|---|---|---|
| EP | 0552949 B1 | 7/1993 |
| ES | 263-394/9 | 5/1984 |
| FR | 2580926 | 11/1986 |
| FR | 2697996 | 5/1994 |
| FR | 2721200 | 12/1995 |
| FR | 2751528 | 1/1998 |
| IT | 1129191 | 6/1986 |

OTHER PUBLICATIONS

Krushell et al., Range of Motion in Contemporary Total Hip Arthroplasty, The Journal of Arthroplasty, vol. 6, No. 2, Jun. 1991.

Egan et al., Biomechanics of Total Hip Arthroplasty, Seminars in Arthroplasty, vol. 4, Oct. 1993.

Herrlin et al., Range of Motion Caused by Design of the Total Hip Prosthesis, Acta Radiological 29 (1988).

Barrack et al., Instability After Major Joint Replacement, Orthopedic Clinics of North America, vol. 32, No. 4, Oct. 2001.

Prosthetic Design and Outcome in Total Hip Arthroplasty, The Journal of Bone & Joint Surgery, vol. 83-A, No. 5, May 2001.

McGrory, Effect of Femoral Offset on Range of Motion and Abductor Muscle Strength After Total Hip Arthroplasty, Journal of Bone Joint Surgery, vol. 77-B, No. 6, Nov. 1995.

Gondi et al., Impingement After Total Hip Arthroplasty Related to Prosthetic Component Selection and Range of Motion, Journal of the Southern Orthopaedic Association, vol. 6, No. 4, Winter 1997.

Barrack et al., The Effect of Component Design on Range of Motion to Impingement in Total Hip Arthroplasty, AAOS Instructional Course Lectures, vol. 50, 2001.

Range of Motion of the Hip, The Orthopaedic Forum, vol. 82-A, No. 11, Nov. 2000.

Huo et al., Custom-Designed Femoral Prostheses in Total Hip Arthroplasty Done with Cement for Severe Dysplasia of the Hip, The Journal of Bone and Joint Surgery, vol. 75-A, No. 10, Oct. 1993.

Long-Term Results of Total Hip Arthroplasty with a Cemented Custom-Designed Swan-Neck Femoral Component for Congenital Dislocation or Severe Dysplasia, DiFazio et al., Journal of Bone and Joint Surgery, vol. 84-A, No. 2, Feb. 2002.

Zimmer Modular Revision (ZMR) Hip System.

Zimmer Revision Taper Hip Prosthesis.

Portland Orthopaedics advertisement for Margron Hip Replacement System. Copyright 2002.

Whiteside Biomechanics Quatroloc Femoral System Surgical Procedures manual, (believed to have been offered for sale, publicly used, and/or published prior to filing date of the present application).

Whiteside Biomechanics, Inc. Quatroloc 510(k) Summary, Aug. 7, 1997.

Wright Medical Technology, Profemur Total Hip System catalog (date unknown; believed to have been offered for sale, publicly used, and/or published prior to the filing date of this application).

Wright Medical Technology, Profemur Z Total Hip System Surgical Technique, (author unknown; believed to have been offered for sale, publicly used, and/or published prior to the filing date of this application).

Wright Medical Technology, Profemur Total Hip System Modular Neck Technical Monograph, (author unknown; believed to have been offered for sale, publicly used, and/or published prior to the filing date of this application).

Orthoplant, Ostroprovit Adapter System, (author unknown; believed to have been offered for sale, publicly used, and/or published prior to the filing date of this application).

Zimmer Modular Revision, (author unknown; believed to have been offered for sale, publicly used, and/or published prior to the filing date of this application).

Toni, A. et al., Anatomic cementless total hip arthroplasty with ceramic bearings and modular necks: 3 to 5 years follow-up, *Hip International*, 11(1): 1-17, 2001.

Traina, F. et al., Modular Neck Primary Prosthesis: Experimental and Clinical Outcomes, Scientific Exhibit at the 71st AAOS Annual Meeting, Mar. 10-14, 2004.

Modular Anatomical Hip Prothesis, A.C.S.E.L. II, a Progressive System Catalog, (author unknown; believed to have been offered for sale, publicly used, and/or published prior to the filing date of this application).

* cited by examiner

ANTI-IMPINGEMENT FEMORAL PROSTHESES

Matter enclosed in heavy brackets [ ] appears in the original patent but forms no part of this reissue specification; matter printed in italics indicates the additions made by reissue.

REFERENCE TO RELATED APPLICATIONS

This application is a continuation of U.S. patent application Ser. No. 09/804,856, filed Mar. 13, 2001, now U.S. Pat. No. 6,383,225 which is a continuation of U.S. patent application Ser. No. 09/411,738, filed Oct. 1, 1999, now U.S. Pat. No. 6,200,350, the entire content of both applications being incorporated herein.

FIELD OF THE INVENTION

This invention relates generally to orthopaedic surgery and, more particularly, to a proximal femoral prosthesis facilitating an enhanced range of motion.

BACKGROUND OF THE INVENTION

In total hip arthroplasty, the defective head and neck of the proximal femur are removed and replaced with a prosthetic element. Although extramedullary units are available, intramedullary prostheses are more commonly employed, which feature an elongated stem adapted for insertion and fixation within the femoral canal.

FIG. 1 is a generalized representation of a prior-art proximal femoral endoprosthesis. A head portion 102 having an outer surface 103 which is at least partially hemispherical is joined to a stem 106 through a neck portion 104. Such interconnections may be permanent and integral, or modular connections may be used in conjunction with tapered metal joints, for example.

The stem 106 defines a first axis 108 which is aligned more or less to the longitudinal axis of the femur, depending upon the style of the particular implant. The neck 104 defines a second axis 110 which intersects with the first axis 108 at a neck/shaft angle which may be varied in accordance with the physiology of the recipient or the desires of a given manufacturer. A typical neck/shaft angle $\alpha$ is on the order of 135°. The offset, or distance from the head portion to the axis of the stem, may also varied to achieve a desired result. A number of other variations exist, including cemented versus cementless interfaces, curved versus straight stem profiles, differently sized balls, and so forth.

In all existing configurations, the neck is straight or, in some cases, curved upwardly (or proximally) away from a plane transverse to the axis of the stem. That is to say, a centroid drawn from a central region 112 of the head 102 to a point of intersection 111 with the stem axis 108 is straight or occasionally curved to create a convex neck surface in existing designs. Such a configuration has several shortcomings. For one, as manufacturers decrease the neck-shaft angle $\alpha$ to improve offset and abductor tension, patients lose movement in flexion secondary to impingement of the neck on the acetabular component.

SUMMARY OF THE INVENTION

This invention resides in proximal femoral prostheses which minimize impingement, thereby affording an enhanced range of motion as compared to existing devices. Broadly, the central portion of the neck of the inventive prosthesis is oriented downwardly relative to a straight line drawn between the ball portion and the point of interconnection to the exposed portion of the stem. Such a configuration reduces impingement in flexion/internal rotation and extension/external rotation, assuming an appropriately placed acetabular component. In the preferred embodiment, the neck is curved between the head and the neck, though, in alternative embodiments, the neck may be provided in straight and/or modular segments. The invention is compatible with neck-shaft angles, offsets, head sizes, and other dimensions commonly designated with respect to available implants. The neck may also be curved in the transverse plane adding increased anteversion or retroversion to the neck-shaft relationship.

DETAILED DESCRIPTION OF THE INVENTION

Figure 1:
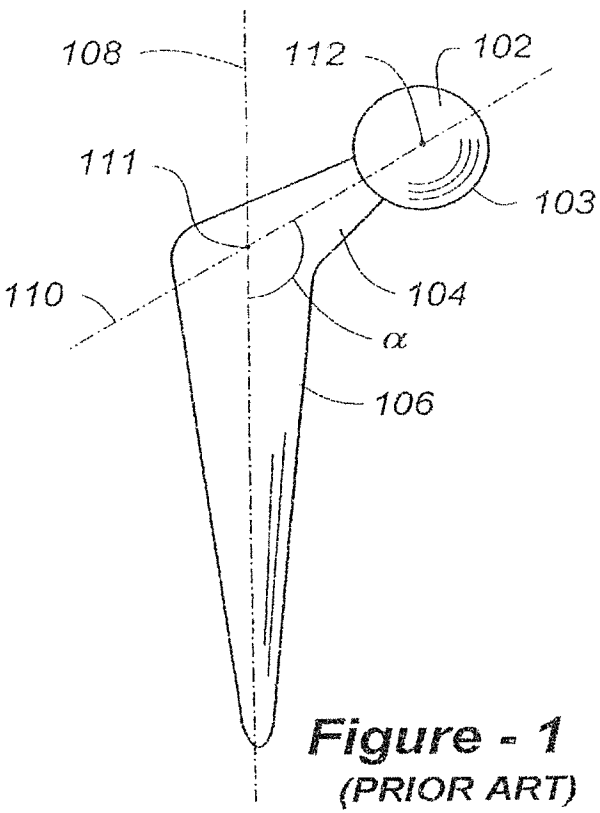
Figure - 1 (PRIOR ART)
FIG. 1 is a front-view drawing of a prior-art proximal femoral endoprosthesis having a straight neck.

Having discussed the prior-art design of FIG. 1 in the Background of the Invention, reference will now be made to FIG. 2, which illustrates a preferred embodiment of the invention from a front-view perspective. As with existing devices, a femoral endoprosthesis according to the invention features a stem (206), head or ball portion (202) and a neck 204. For the sake of reference, a straight line 210 has been drawn from a point 211 intersecting the axis of the stem and the center 212 of the ball. In contrast to existing devices, wherein the neck is either straight or curved upwardly or proximally relative to the straight line, the neck 204 of a prosthesis utilizing the invention curves downwardly or distally relative to the line establishing a superior concave surface to reduce impingement of the central region of the neck on the acetabular component. The "central region" ("cr") is defined as the region of the neck between a line parallel to "s" along the most medial aspect of the stem ("$s_1$") and a line parallel to "s" and tangent to the lateral outer surface of the head closest to the superior surface of the neck ("$s_2$").

More particularly, the centroid of the neck, which in this case is defined as the centerline 220 through the center of each cross section taken along the body of the neck is, at least the mid section (222), below or distal to the straight line 210 between the intersection 211 with the axis 208 of the of the stem and the center 212 of the ball.

Not each point of the neck according to the invention need be below or distal to the straight line 210, but rather, only a portion of the centerline. If one considers that the neck 204 includes a first portion 201 connected to the stem 206, and a second portion 203 connected to the head 202, if one draws a line tangent to the curve 220 at the point "X" and a second line tangent to the curve 210 at the point "C," they will intersect at a point "P," and it at least this point "P" which is distal or below the straight line 210. In addition, although the neck according to the invention is said to be curved, it need not be a smooth, continuous curve as shown in FIG. 2, but rather, may be made up of one or more straight segments such as 302 and 304, as shown in FIG. 3. In this configuration, the first segment 301 includes a substantially straight longitudinal axis 302 ("$n_1$"), which intersects with the longitudinal axis ("s") of the stem 300 at an angle $a_1$. The second segment of the neck, associated with connection with a head 305, includes a second substantially straight longitudinal axis 304 ("$n_2$"), which intersects with $N_1$ at the point "p," without having to straight tangents to a curve. Note also, that in both of the embodiments of FIGS. 2 and 3, if one extends the axis of the second segment of the neck associated with interconnection to the head or ball portion, the angle formed between this line and the stem "s" ("$a_2$"), is at all times greater than the angle $A_1$ formed between the axis of the first segment associated with interconnection to the stem, and the longitudinal axis of the stem "s." This is contrast to existing devices, wherein these two angles are either the same, or wherein $a_1$ is greater than $a_2$, indicating that the neck curves downwardly as opposed to upwardly, thereby potentially exacerbating problems with impingement.

Figure 4:
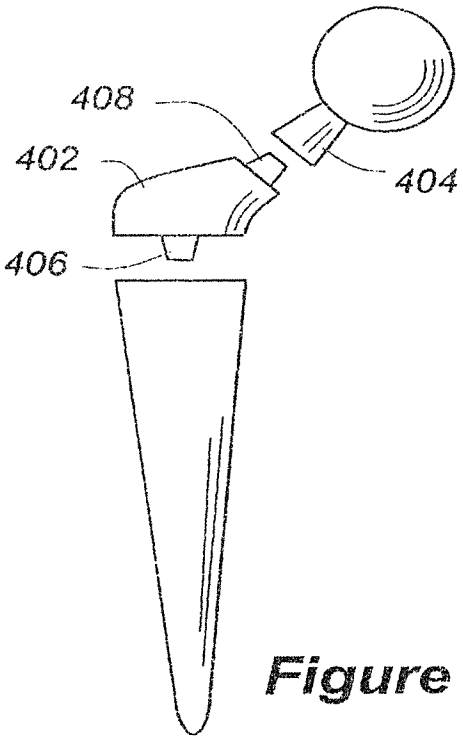
FIG. 4 is a front-view drawing of a further alternative embodiment of the invention having a modular neck.

Furthermore, a prosthesis having a neck according to the invention need not be solid and integral but instead, may utilize modular segments. FIG. 4 is representative, wherein a module 402 fits to a stem through a joint having post 406, and a head portion 404 attaches to the module 402 though a mating connector 408. Other arrangements are possible, including additional and differently configured modules, so long a least a portion of the centroid through the finally assembled structure is below or distal to a straight line from the center of the ball to a point of intersection with the axis of the stem.

Figure 6:
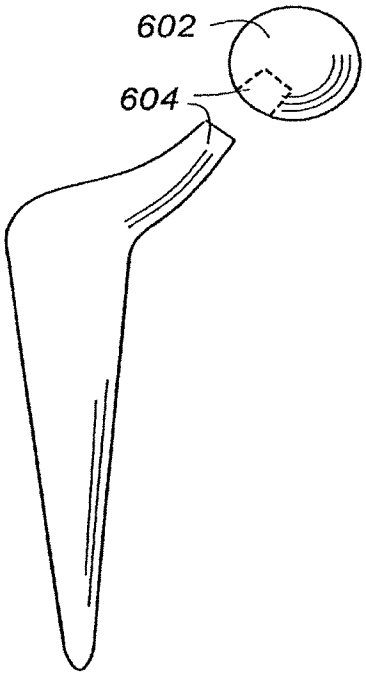
FIG. 6 illustrates yet a different embodiment, wherein a modular ball component connects to an integral neck/stem.
Figure 5:
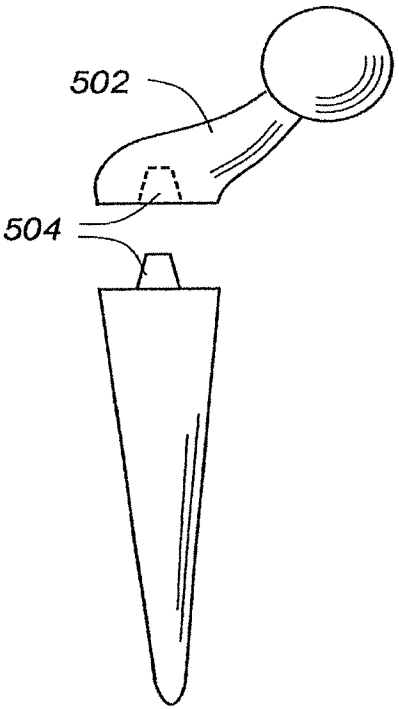
FIG. 5 is a front-view drawing of a different alternative embodiment of the invention including a modular connection between an anti-impinging neck and implant.

FIG. 5 illustrates a different alternative embodiment, wherein an anti-impinging neck component 502 is integral with a ball portion, but connects to a stem through a joint 504. FIG. 6 illustrates a different configuration, wherein the neck and stem are integral, but a modular ball 602 connects to an end of the stem through the joint 604.

Figure 2:
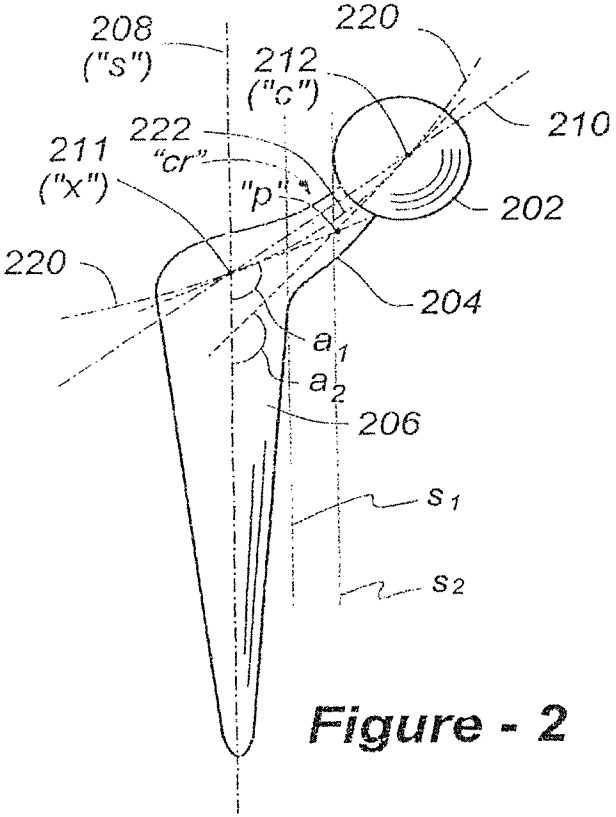
FIG. 2 is a front-view drawing of a proximal femoral endoprosthesis according to the invention having a curved neck which reduces impingement.
Figure 3:
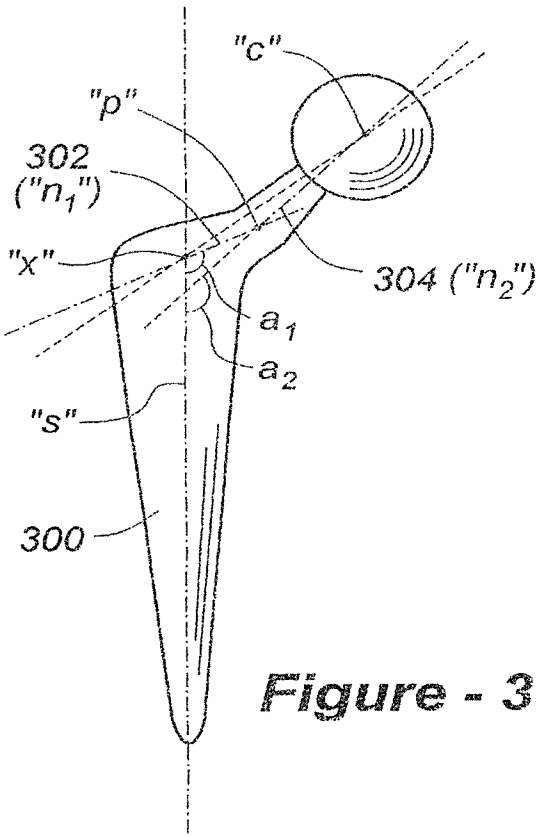
FIG. 3 is a front-view drawing of an alternative embodiment of the invention having an anti-impingement neck provided in multiple straight segments.
Figure 7A:
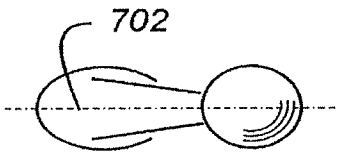
FIG. 7A is a top-view drawing illustrating how an anti-impinging neck may be curved only within the coronal plane through the head, neck and stem.
Figure 7B:
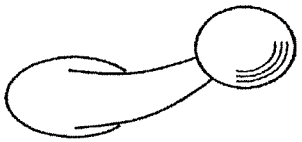
FIG. 7B illustrates how a neck according to the invention may be curved apart from, or in addition to a curve in the coronal plane so as to avoid impingement.
Figure 7C:
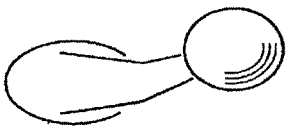
FIG. 7C illustrates how "curves" relative to the coronal plane need not be smooth and continuous, but may be piecewise.

Although a femoral prosthesis according to the invention may be curved only in the coronal plane, which may be defined as that plane which intersects the central portions of the head, neck and stem, as shown in FIG. 2, in particular, the neck according to the invention may also be curved relative to the coronal plane whether in a simple or compound configuration. Reference is made to FIG. 7A, which shows a top-down view of a femoral prosthesis which, according to the invention, would have the ball portion curve upwardly and away from the paper in a manner which is different from prior art configurations. But in addition to such an upward curve in the coronal plane 702, in the neck may also be curved relative to the coronal plane, whether or not it is also curved within the coronal plane. That is, the curve of the neck may be piecewise as opposed to continuous, as shown in FIG. 7C.

I claim:

1. An anti-impingement femoral prosthetic component, comprising:

a stem having a distal portion adapted for placement within an intramedullary canal, a proximal end which remains externally exposed subsequent to fixation, and a longitudinal axis, "s";

a head having a center configured to co-act with a corresponding acetabular component; a coronal plane being defined as the plane which intersects "s" and the center of the head; a neck connecting the stem to the head, the neck having superior and inferior surfaces and a central region defined as the region of the neck between a line parallel to "s" along the most medial aspect of the stem and a line parallel to "s" and tangent to the lateral outer surface of the head closest to the superior surface of the neck; and wherein the superior [and inferior surfaces] *surface* of the neck [define] *defines* smooth, continuous curves in the coronal plane, *and the inferior surface of the neck is curved or angled in the coronal plane,* with the apex of each [curve] *surface* being oriented distally, establishing a superior concave surface to reduce impingement of the central region of the neck on the acetabular component, thereby facilitating an enhanced range of motion in flexion/internal rotation and extension/external rotation.

2. The anti-impingement femoral prosthetic component of claim 1, including different head sizes, stem offsets and neck angles to accommodate varying patient physiologies.

3. The femoral prosthetic component of claim 1, wherein the neck has a radius of the curvature with a center located proximal to the neck.

4. The femoral prosthetic component of claim 1, wherein the head is modularly connected to the neck.

5. The femoral prosthetic component of claim 1, wherein the neck is modularly connected to the stem.

6. The femoral prosthetic component of claim 1, wherein the neck is modularly connected to the body portion.

7. The femoral prosthetic component of claim 1, wherein the neck is further angled or curved outside the coronal plane to change the anteversion or retroversion of the head relative to femur.

8. The femoral prosthetic component of claim 1, wherein the body portion may be rotated relative to the stem to change the anteversion or retroversion of the neck or head.

* * * * *